(12) United States Patent
Sawa et al.

(10) Patent No.: US 6,425,886 B1
(45) Date of Patent: Jul. 30, 2002

(54) SYRINGE AND APPARATUS FOR MANUFACTURING THE SAME

(75) Inventors: Teiichirou Sawa, Osaka; Hirotaka Nishida; Taiji Horita, both of Ibaraki, all of (JP)

(73) Assignees: Maeda Sangyo Co., Ltd.; Taisei Kako Co., Ltd., both of Osaka (JP)

( * ) Notice: Subject to any disclaimer, the term of this patent is extended or adjusted under 35 U.S.C. 154(b) by 190 days.

(21) Appl. No.: 09/614,349

(22) Filed: Jul. 12, 2000

Related U.S. Application Data (62) Division of application No. 09/296,345, filed on Apr. 22, 1999.

(30) Foreign Application Priority Data

Apr. 28, 1998 (JP) .......................................... 10-119219

(51) Int. Cl.[7] ................................................ A61M 5/00
(52) U.S. Cl. ......................... 604/230; 206/571; 141/11
(58) Field of Search ................................ 604/187, 218, 604/228, 230; 264/219, 519, 524, 525; 222/282; 206/570, 571; 141/11; 29/422, 434; 433/90

(56) References Cited

U.S. PATENT DOCUMENTS 4,703,781 A * 11/1987 Meyer et al. ................. 141/11
5,282,792 A * 2/1994 Imbert ......................... 206/571
5,953,884 A * 9/1999 Lawecki et al. .............. 141/11

* cited by examiner

Primary Examiner—Anhtuan T. Nguyen
(74) Attorney, Agent, or Firm—Jordan and Hamburg LLP (57) ABSTRACT

The present invention provides a syringe including a tubular barrel. The tubular barrel has an open proximal end, a distal end with a fluid expelling passage defined therein, and a barrel chamber. A seal is disposed within the barrel chamber a predetermined distance away from the open proximal end in fluid-tight and axially-sliding engagement with the barrel chamber, so that fluid held in the barrel chamber between the fluid expelling passage and the seal can be expelled from the barrel chamber to the outside via the fluid expelling passage by sliding the seal towards the fluid expelling passage. The seal defines at least two diametrically enlarged portions at axially spaced apart portions of the seal so as to be respectively in abutment with the inner wall of the barrel chamber and a concave portion between adjacent diametrically enlarged portions of the at least two diametrically enlarged portions for defining a clearance relative to the inner wall of the barrel chamber, in which lubricant film exists at interfaces between the at least two diametrically enlarged portions of the seal and the inner wall of the barrel chamber, and lubricant is filled in the clearance. The present invention also provides a syringe assembly and an apparatus for manufacturing the syringe having the above arrangement.

1 Claim, 5 Drawing Sheets

SYRINGE AND APPARATUS FOR MANUFACTURING THE SAME

This is a division, of application Ser. No. 09/296,345, filed Apr. 22, 1999.

BACKGROUND OF THE INVENTION

1. Field of the Invention

The present invention relates to a syringe and a syringe assembly having such an arrangement that a medical fluid held in a barrel is expelled from the barrel via a fluid expelling passage of the barrel, as well as an apparatus for manufacturing the same.

2. Discussion of the Background

Generally, a syringe assembly includes:

a tubular barrel having an open proximal end through which a medical fluid is introduced into the barrel, and a distal end with a fluid expelling passage through which the medical fluid held in the barrel is expelled into the body of a person to be treated;

an elastic seal disposed within a barrel chamber in fluid-tight and axially-sliding engagement with the inner wall of the chamber; and a plunger rod having a proximal end projecting proximally from the proximal end of the barrel, and a distal end interconnected to the seal, so that the medical fluid held in the barrel chamber is expelled from the barrel chamber via the fluid expelling passage by sliding the seal by using the plunger rod.

In the above arrangement, it is necessary to slide the seal within the barrel chamber as maintaining the seal in fluid-tight engagement with the inner wall of the barrel chamber. To achieve high slidability of the seal relative to the inner wall of the barrel chamber, a conventional syringe assembly employs lubricant such as a silicon oil, which is applied to the entire surface of the inner wall of the barrel chamber so as to form a silicon film.

Although the silicon oil is not harmful even if it is introduced into the body, it is preferable to limit the quantity of the silicone oil introduced into the body. However, the conventional syringe of the above arrangement causes the medical fluid filled in the barrel chamber to constantly contact the silicon film, resulting in a high possibility of elusion of silicon into the medical fluid. Particularly, a pre-filled syringe assembly, which is shipped with the medical fluid therein, causes the medical fluid to contact the silicon film for a prolonged period of time, resulting in increasing the possibility of the elusion of silicon. Further, unlike a barrel formed from glass, a barrel formed from plastic may increase the possibility of the elusion of the silicon into the medical fluid, since silicone cannot be baked on the plastic barrel.

Therefore, the present invention has been conceived to solve the above problems in a syringe of the type that includes the tubular barrel, the seal held within the barrel chamber in fluid-tight and axially sliding engagement with the inner wall of the barrel chamber of the barrel, so that a fluid held in the chamber is expelled from the barrel chamber by sliding the seal. It is an object of the present invention to provide a syringe and a syringe assembly capable of preventing lubricant from being introduced into a fluid or a fluid forming drug held in the barrel chamber, as maintaining the seal in fluid-tight and sliding engagement with the inner wall of the barrel chamber.

It is another object of the invention to provide an apparatus for manufacturing the syringe and the syringe assembly of the above arrangement.

SUMMARY OF THE INVENTION

In accordance with the present invention, there is provided a syringe including a barrel and a seal being forced into a barrel chamber of the barrel, the seal defining at least two diametrically enlarged portions at axially spaced apart portions of the seal so as to be respectively in abutment with the inner wall of the barrel and a concave portion between adjacent diametrically enlarged portions of the at least two diametrically enlarged portions for defining a clearance relative to the inner wall of the barrel chamber, in which (1) lubricant does not exist on the inner wall of the barrel chamber of the barrel with the exception of the portion of the inner wall at which the seal is held, (2) lubricant film exists only at interfaces between the at least two diametrically enlarged portions of the seal and the inner wall of the barrel chamber, and (3) lubricant is filled in the clearance between the inner wall of the barrel chamber and the concave portion. This arrangement can effectively prevent fluid held in the barrel from contacting lubricant, thereby maintaining fluid-tight characteristic and slidability of the seal and simultaneously preventing the mixture of the lubricant into the fluid.

It may be preferable to employ the arrangement where the lubricant film does not exist at an interface between the inner wall of the barrel and one diametrically enlarged portion that is distally positioned among the at least two diametrically enlarged portions of the seal. Thereby, the mixture of the lubricant into the fluid can more effectively be prevented.

It may be possible to provide a syringe assembly by equipping the syringe with a plunger rod having a proximal end projecting proximally from the proximal end of the barrel, and a distal end interconnected to the seal.

When used in a pre-filled syringe assembly, the syringe of the present invention produces a more remarkable effect as compared with the conventional syringe.

The apparatus of the present invention is configured so that a projecting portion of a lubricant applying unit is plunged into the barrel chamber of the syringe, and under this state, the seal having the diametrically enlarged portions onto which the lubricant is applied and the concave portion into which lubricant is filled can be forced into the barrel chamber. Thereby, it is possible to effectively manufacture the syringe having the arrangement where the lubricant film exists only at the interfaces between the inner wall of the barrel chamber and the diametrically enlarged portions of the seal, and the lubricant is filled in the clearance.

BRIEF DESCRIPTION OF THE DRAWINGS

The above, and other objects, features and advantages of the present invention will become apparent from the detailed description thereof in conjunction with the accompanying drawings wherein.

FIG. 4(a) to FIG. 4(d) respectively show steps of manufacturing the syringe of FIG. 1.

DETAILED DESCRIPTION OF THE PREFERRED EMBODIMENT

EMBODIMENTS

The preferred embodiments of a syringe in accordance with the present invention will be hereinafter described with reference to the accompanying drawings.

Embodiment 1

Figure 1:
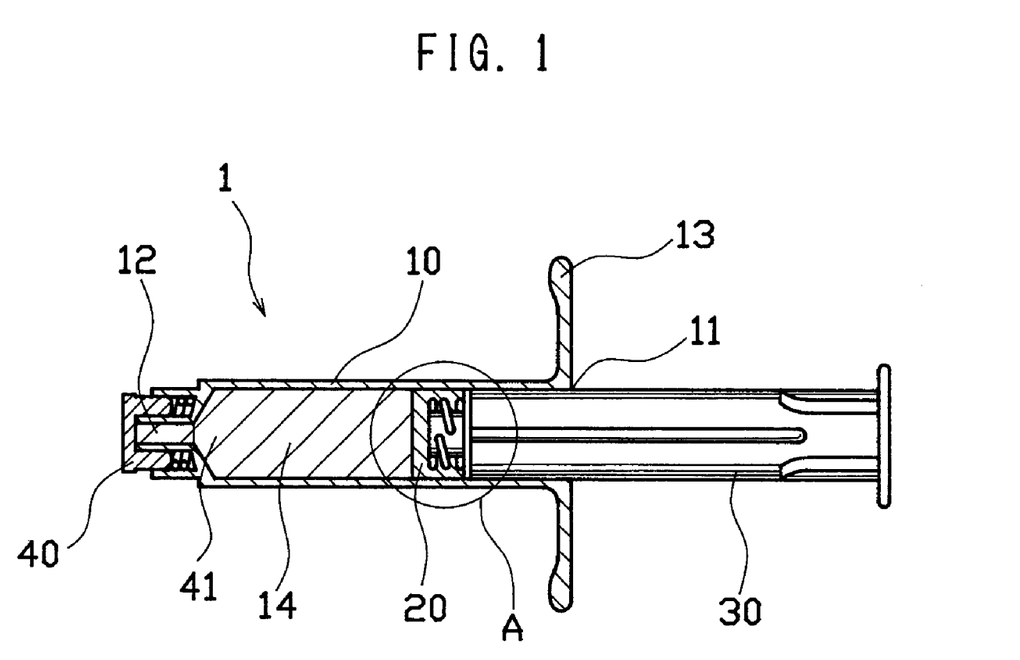
FIG. 1 is a longitudinal cross section of a syringe in accordance with a first embodiment of the present invention.
Figure 2:
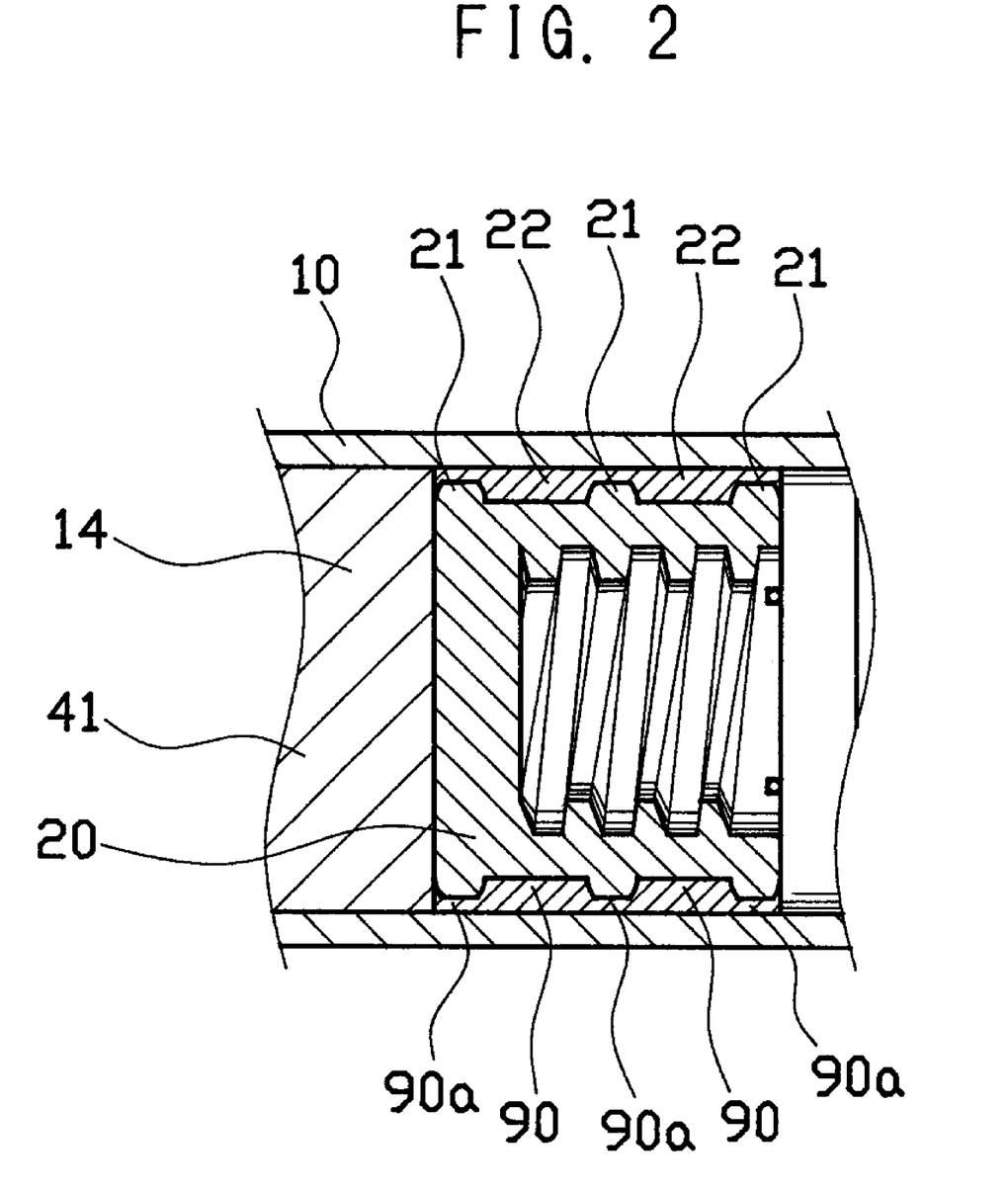
FIG. 2 is an enlarged view of a portion defined by the circle of A in FIG. 1.

FIGS. 1 and 2 are respectively a longitudinal cross section of a syringe in accordance with this embodiment, and an enlarged view of a portion defined by the circle of A in FIG. 1.

As illustrated in FIG. 1, the syringe 1 of this embodiment includes a tubular barrel 10 having an open proximal end 11, and a distal end with a fluid expelling passage 12 defined therein, a cylindrical seal 20 held within a barrel chamber a predetermined distance away from the open proximal end 11 in fluid-tight and axially-sliding engagement with the inner wall of the barrel chamber. By sliding the seal towards the fluid expelling passage 12, a fluid held in the barrel chamber between the fluid expelling passage 12 of the barrel and the seal 20 is expelled from the barrel chamber to the outside via the fluid expelling passage 12.

The barrel 10 may preferably be provided at its proximal end with a flange 13 radially and outwardly projecting from the open proximal end 11 and at its distal end with an arrangement enabling a piecing element such as a needle cannula to be attached to the distal end of the barrel 10. Further, the syringe 1 may preferably be provided with a plunger rod 30 having a proximal end projecting proximally from the proximal end of the barrel, and a distal end interconnected to a proximal end of the seal so as to form a syringe assembly. In FIG. 1, reference numerals 40 and 41 respectively represent a cap for sealing a medical fluid and the medical fluid, both of which are prepared for a pre-filling syringe.

As illustrated in FIG. 2, the seal 20 defines at least two diametrically enlarged portions 21 at axially spaced apart portions of the seal, and a concave portion 22 positioned between adjacent diametrically enlarged portions of the at least two diametrically enlarged portions. The diametrically enlarged portions each are larger in diameter than the inner diameter of the barrel chamber 14 so as to become in abutment with the inner wall of the barrel chamber 14 under compressed and deformed states, thereby enabling the seal to exhibit a fluid-tight characteristic. On the other hand, the concave portion 22 is smaller in diameter than the inner diameter of the barrel chamber 14, and hence defines a clearance between the concave portion 22 of the seal and the inner wall of the barrel chamber 14. The concave portion 22 may be in the form of an annular groove extending around the circumferential periphery of the seal, or a plurality of cavities defined around the circumferential periphery of the seal with predetermined spaces. However, considering slidability and ease of manufacturing, it is preferable to employ an annular concave portion as illustrated in FIGS. 1 and 2. In FIG. 2, each diametrically enlarged portion 21 is illustrated as being diametrically smaller than the barrel chamber 14 so as to clearly show the existence of lubricant film 90a at interfaces between the diametrically enlarged portions and the inner wall of the barrel chamber 14. However, as described above, the diametrically enlarged portions 21 are radially compressed into tight engagement with the inner wall of the barrel chamber 14 with the lubricant film 90a existing at the interfaces therebetween.

In accordance with this embodiment, where the lubricant film 90a exists only at the interfaces between the inner wall of the barrel chamber 14 and the circumferential peripheries of the diametrically enlarged portions 21, and a lubricant 90 is filled in the clearance defined by the concave portion 22 of the seal and the inner wall of the barrel chamber 14, it is possible to prevent the medical fluid held in the barrel from contacting the lubricant, and simultaneously improve the slidability of the seal 20.

Specifically, in accordance with a conventional syringe having an arrangement where the seal with lubricant applied onto the entire surface of the inner wall thereof is forced into the barrel chamber, the medical fluid held in the barrel chamber constantly contacts the lubricant, resulting in a high possibility of the elusion of the lubricant into the medical fluid. Particularly, a barrel formed from plastic increases the possibility of the elusion of the lubricant since the lubricant cannot be baked on the surface of the barrel formed from plastic.

Contrarily, in accordance with the syringe 1 of this embodiment, where the lubricant is not applied onto the inner wall of the barrel chamber with the exception of the portion where the seal 20 is held, and the lubricant film exists only at the interfaces between the inner wall of the barrel chamber and the diametrically enlarged portions of the seal, it is possible to effectively prevent the elusion of the lubricant into the medical fluid, and simultaneously improve the slidability of the seal.

Figure 3:
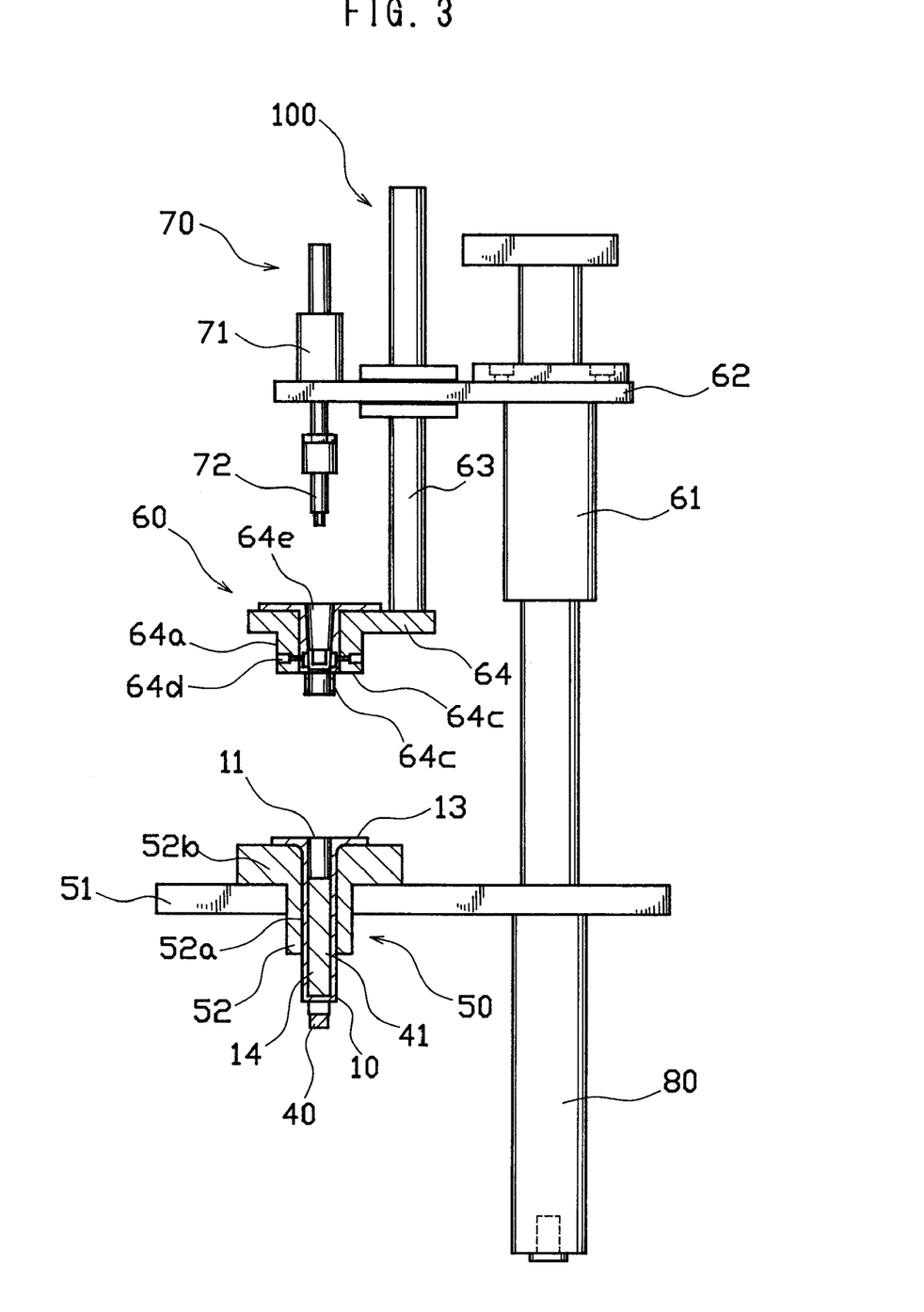
FIG. 3 is a schematic view of an apparatus for manufacturing the syringe of FIG. 1.

Next, an apparatus for manufacturing the syringe 1 of this embodiment will be described with reference to FIG. 3. FIG. 3 is a schematic view of the apparatus. The apparatus 100 includes a barrel retaining unit 50, a seal detent unit 60 and a thrusting unit 70.

The barrel retaining unit 50 includes a first supporting plate 51 horizontally supported on a vertically standing main rod 80, and a retaining member 52 supported on the first supporting plate 51. The first supporting plate 51 may be supported on a frame (not shown).

The retaining member 52 includes a tubular portion with a through-hole 52a therein extending in parallel with the axis of the main rod 80, and a flange 52b extending horizontally from the tubular portion. The barrel 10 is inserted into the through-hole 52a to be retained therein so that the barrel chamber 14 is positioned in parallel with the main rod 80, and the open proximal end 11 of the barrel 10 is upwardly directed. The barrel retaining member 52 is supported on the first supporting plate 51 via the flange 52b.

The seal detent unit 60 disposed above the barrel retaining unit 50 includes a main piston 61 reciprocable along the main rod 80, a second supporting plate 62 horizontally supported on the main piston 61, an intermediate rod 63 vertically supported on the second supporting plate, and a detent member 64 supported above the retaining member 52 and below the second supporting plate 62 via the intermediate rod.

The detent member 64 includes a trunk portion 64a, a diametrically smaller tubular portion 64b extending downwardly from the trunk portion 64b with a stepped portion 64c, and defines therein a through-hole 64e that is coaxially alignable with the barrel chamber 14 of the barrel to be retained within the retaining member 52, and includes at its lower side a trunk portion 64a that is accompanied by a decrease in diameter at a stepped portion 64c and terminates in a diametrically smaller tubular portion 64b. The diametrically smaller tubular portion 64b has the outer diameter smaller than the inner diameter of the barrel chamber 14, and hence is capable of plunging into the barrel chamber 14 via downward movement of the main piston 61.

The inner wall of the detent member 64 may preferably have a tapered cross section so that the through-hole 64e becomes smaller in diameter as it advances downwards, enabling the detent member 64 to hold the seal 20 at a predetermined detent position within the through-hole 64e. The trunk portion 64a defines therein a passage 64d in communication between the detent position of the through-hole and the outside of the detent member 64 so that lubricant can be fed from the outside via the passage to be applied on the circumferential periphery of each diametrically enlarged portion 21 of the seal and to be filled in the concave portion 22 of the seal.

The thrusting unit 70 includes a subsidiary rod 71 supported on the second supporting plate 62 so as to be positioned above the seal detent unit 60, and a thrusting member 72 reciprocable along the subsidiary rod.

The subsidiary rod 71 is disposed so as to be coaxially aligned with the through-hole 64e of the detent member 64, and more specifically with the barrel chamber 14 of the barrel to be retained within the retaining member 52. The thrusting member 72 has a lower portion with its outer diameter smaller than the outer diameter of the seal 20, so that the seal 20 held within the detent member 64 can be moved downwards and forced out of the detent member 64 via an opening of the diametrically smaller tubular portion 64b by moving the thrusting member 72 downwards.

The operational steps of the apparatus having the above arrangement will be hereinafter described with reference to FIGS. 4(a) to 4(d), which show the respective steps of manufacturing the syringes by using the apparatus. First, the seal 20 is positioned at the detent position of the through-hole 64a of the detent member 64. Lubricant is, then, applied to the circumferential periphery of each diametrically enlarged portion 21 of the seal, and filled within the concave portion 22 (FIG. 4(a)).

The main piston 61 is, then, slid downwards to move the entirety of the seal detent unit 60 downwards, thereby plunging the diametrically smaller tubular portion 64b of the detent member into the barrel chamber 14. The thrusting unit 70 is then slid downwards to thrust the seal 20 to the lower end of the diametrically smaller tubular portion 64b via the thrusting member 72 (FIG. 4(b)).

Figure 4A:
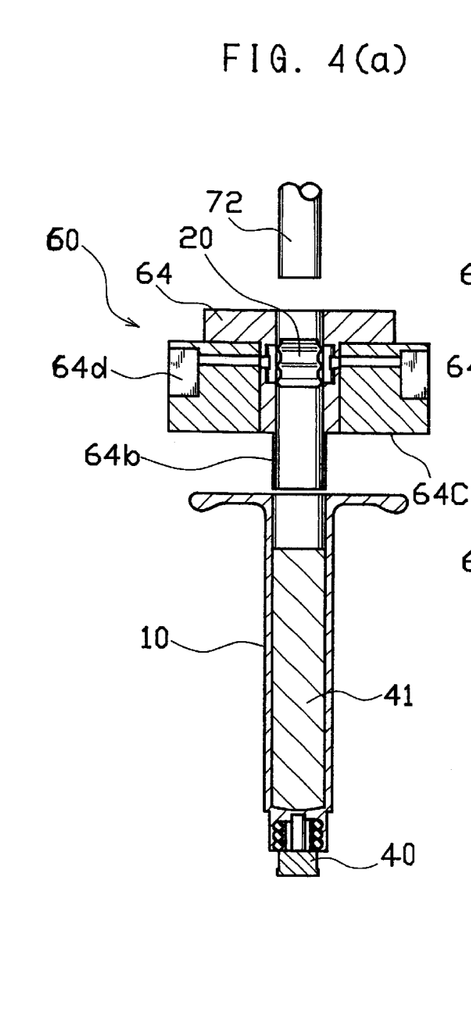
Figure 4B:
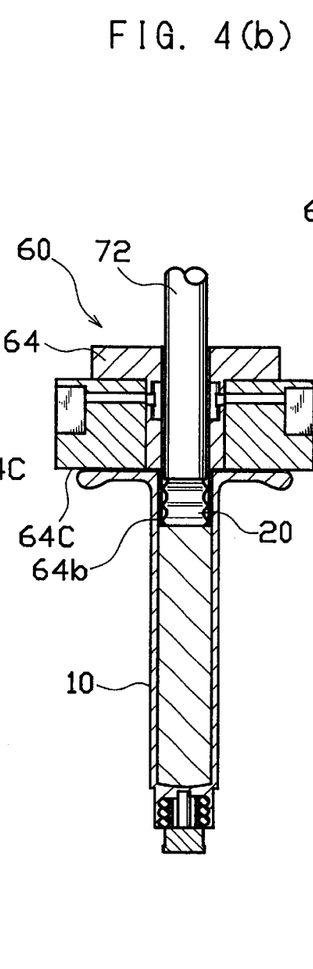
Figure 4C:
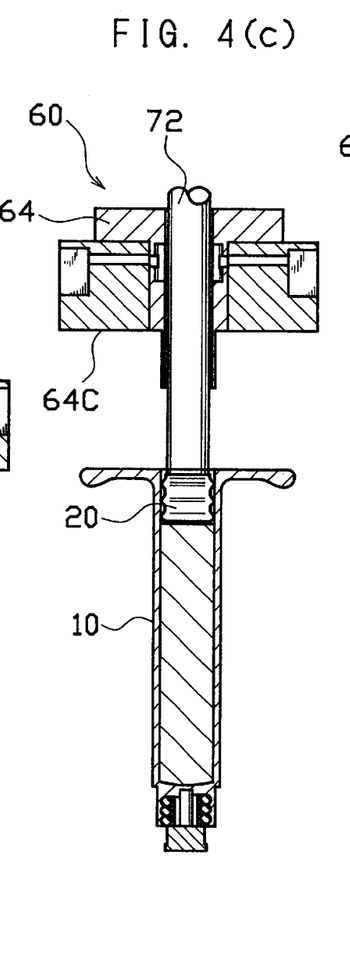

The seal detent unit 60 is, then, moved upwards as the thrusting member 72 remains in the position of FIG. 4(b), so that the seal 20 is forced into the barrel chamber 14 (FIG. 4(c)).

Figure 4D:
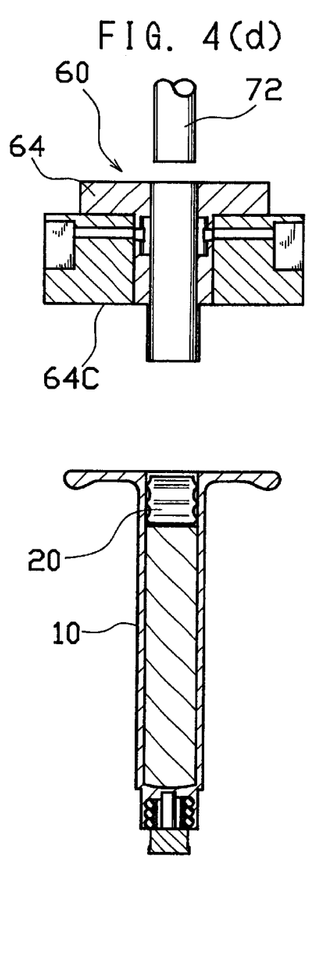

The main piston 61 is, then, moved upwards to move the thrusting member 72 upwards (FIG. 4(d)), so that the barrel 10 with the seal 20 therein can be withdrawn from the barrel retaining unit 50.

In accordance with this apparatus, it is possible to effectively manufacture the syringe having an arrangement where the seal 20 has been forced into the barrel chamber 14 and held within the barrel chamber a predetermined distance away from the open proximal end 11 of the barrel 10, lubricant is not applied onto the inner wall of the barrel chamber 14 with the exception of the portion where the seal 20 is held, the lubricant film 90a exists only at the interfaces between the inner wall of the barrel chamber 14 and the diametrically enlarged portions 21 of the seal, and the lubricant 90 is filled in the clearance defined by the inner wall of the barrel chamber 14 and the concave portion 22 of the seal. Further, in accordance with this apparatus, it is possible to easily vary a seal holding position in the barrel chamber 14 by, for example, varying the length of the diametrically smaller tubular portion 64b of the detent member 64.

In the apparatus of this embodiment, the lower terminal point of the motion of the seal detent unit 60 is regulated by abutment between the stepped portion 64c of the detent member and the upper end of the barrel 10. However, the regulation of the terminal point is not necessarily accomplished by this arrangement, and hence can be accomplished by various arrangements, for example, by attaching a spacer on the first supporting plate 51.

Embodiment 2

Next, a second preferred embodiment of the present invention will be hereinafter described with reference to FIG. 5, in which corresponding or identical parts to those of the first embodiment have been given the same reference characters to omit a detailed description thereof.

Figure 5:
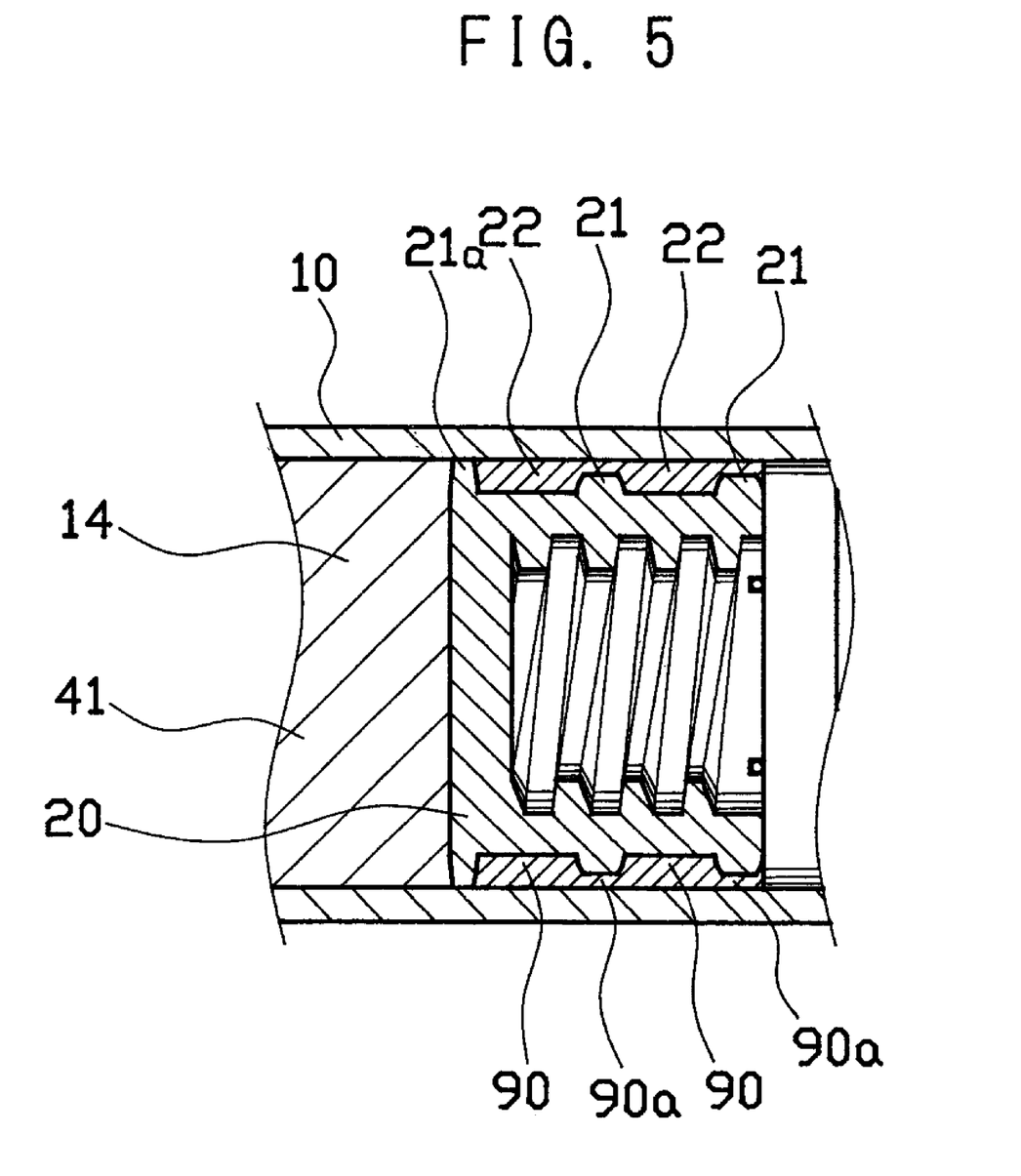
FIG. 5 is a longitudinal cross section of a seal and its vicinity in a syringe in accordance with a second embodiment.

As illustrated in FIG. 5, the syringe of this embodiment is configured and dimensioned so that the lubricant film 90a does not exist at the interface between the circumferential periphery of a diametrically enlarged portion 21a that is distally positioned and the inner wall of the barrel chamber 14. This diametrically enlarged portion 21a may preferably be configured to become thinner, thereby preventing deterioration of the slidability of the seal 20 due to a frictional resistance caused between the circumferential periphery of the diametrically enlarged portion 21a and the inner wall of the barrel chamber 14.

It is to be noted that the diametrically enlarged portion 21a is illustrated in FIG. 5 as being larger in diameter than the other diametrically enlarged portions so as to clearly show the existence of the lubricant film 90a at interfaces between the diametrically enlarged portions 21 and the inner wall of the barrel chamber 14. For the actual application, the seal 20 is preferably configured so that the diametrically enlarged portion 21a becomes slightly larger in diameter than the inner diameter of the syringe, and the other diametrically enlarged portions 21 each become larger in diameter than the diametrically enlarged portion 21a. By this configuration, it is possible to effectively prevent deterioration of the slidability of the seal caused by the diametrically enlarged portion 21a, onto which no lubricant is applied.

Thus, the syringe of this embodiment can prevent the mixture of the lubricant into the medical fluid in a more effective manner as compared with the syringe of the first embodiment, as maintaining the fluid-tight characteristic and maintaining the slidability of the seal 20 to some extent. Specifically, as illustrated in FIG. 5, the diametrically enlarged portion 21a of this embodiment completely isolates the lubricant from the medical fluid, thereby preventing the elusion of the lubricant into the medical fluid.

The apparatus described in the first embodiment can be used in manufacturing the syringe of this embodiment by controlling the detent position of the seal 20 within the detent member 64.

EXAMPLES

The testing was conducted by using the syringes of the above embodiments. The test results will be shown hereinafter.

Example 1

As Example 1, the testing was conducted to measure the number of fragments of a silicone coat as silicone foreign matters that fall into a medical fluid filled in the syringe by shaking or an autoclave treatment. First, the number of foreign matters fallen from the syringe with no silicone coating thereon has been measured so as to eliminate any influences caused by foreign matters excluding silicone. The testing method is as follows:

(1) The syringe with no silicone coating applied thereon is rinsed in running clean water, and then rinsed in running dust-free distilled water; (2) After subjected to dry sterilization, the syringe is cooled to room temperature within a clean bench; (3) After being cooled to room temperature, the syringe is filled with dust-free distilled water, and sealed by forcing the seal into the syringe; (4) The syringe prepared in these manners is vigorously shaken for 1 minute, and the number of foreign matters contained per 10 ml of the dust-free distilled water filled within the syringe was measured; and (5) The average number of the foreign matters was determined by the measurements conducted 12 times in the above manners, and was employed as a reference number.

Next, the testing was conducted to measure the number of fragments of a silicone coat as silicone foreign matters that fall from the syringes of the first and second embodiments. The testing method is as follows:

(1) Each syringe of the first and second embodiments with no silicone coating thereon is rinsed in running clean water, and then rinsed in running dust-free distilled water; (2) After subjected to dry sterilization, each syringe is cooled to room temperature within a clean bench. (3) After being cooled to room temperature, each syringe is filled with dust-free distilled water, and sealed with the seal having silicone applied on the circumferential periphery thereof by forcing this seal into the syringe; (4)-1 For the number of silicone foreign matters after the shaking, each syringe prepared in these manners is vigorously shaken for 1 minute, and the number of foreign matters contained per 10 ml of the dust-free distilled water was measured; (4)-2 For the number of foreign matters after the autoclave treatment, each syringe prepared in these manners is subjected to the autoclave treatment at 121.degree. C. for 30 minutes, and the number of foreign matters per 10 ml of the dust-free distilled water filled in each syringe was measured; and (5) The average number of the foreign matters for each syringe was determined after conducting the measurement twelve times according to the items (4)-1 and (4)-2, and the number of silicone foreign matters fallen from each syringe was determined by deducting the reference number mentioned above from the average number.

The number of the foreign matters measured for the syringes of the first and second embodiments will be shown in TABLES 1 and 2.

Further, as comparative examples, syringes formed from glass with silicone coatings applied onto their respective inner walls were prepared. The numbers of fragments of a silicone coat as foreign matters were measured and determined under the same conditions of the testing as those of this example, and the test results for the comparative examples will also be shown in TABLES 1 and 2. The details of the prepared syringes are as follows:

Sample A: Syringe with a silicone coating formed by baking a silicone solution in concentration of 1% at 300.degree. C. for 2 hours;

Sample B: Syringe with a silicone coating formed by baking a silicone solution in concentration of 3% at 300.degree. C. for 2 hours;

Sample C: Syringe with a silicone coating formed by baking a silicone solution in concentration of 3% at 380.degree. C. for 3 hours;

Sample D: Syringe with a silicone coating formed by baking a silicone solution in concentration of 1% at 380.degree. C. for 2 hours; and Sample E: Syringe with a silicone coating formed by baking a silicone solution in concentration of 1% at 380.degree. C. for 3 hours.

TABLE 1

Number of Foreign Matters Fallen after Shaking

|  | not less than 2 μm | not less than 5 μm | not less than 10 μm | not less than 25 μm | not less than 50 μm |
| --- | --- | --- | --- | --- | --- |
| Embodiment 1 | 0 | 0 | 0 | 0 | 0 |
| Embodiment 2 | 0 | 0 | 0 | 0 | 0 |
| Sample A | 45664 | 10945 | 466 | 1 | 0 |
| Sample B | 68745 | 24973 | 2007 | 7 | 0 |
| Sample C | 102 | 7 | 2 | 0 | 0 |
| Sample D | 11 | 2 | 1 | 0 | 0 |
| Sample E | 12 | 3 | 1 | 0 | 0 |

TABLE 2

Number of Foreign Matters after Autoclave Treatment

|  | not less than 2 μm | not less than 5 μm | not less than 10 μm | not less than 25 μm | not less than 50 μm |
| --- | --- | --- | --- | --- | --- |
| Embodiment 1 | 22 | 7 | 0 | 0 | 0 |
| Embodiment 2 | 0 | 0 | 0 | 0 | 0 |
| Sample A | 14156 | 5281 | 1054 | 40 | 0 |
| Sample B | 8290 | 2195 | 254 | 5 | 0 |
| Sample C | 6109 | 1772 | 492 | 55 | 0 |
| Sample D | 3650 | 1228 | 314 | 37 | 0 |
| Sample E | 4238 | 1551 | 491 | 69 | 0 |

As being apparent from TABLES 1 and 2, although the syringes of glass each having a silicone coating baked on the surface thereof were used for the comparative examples, a considerable number of silicone foreign matters were observed. Particularly, silicone foreign matters fallen from those syringes were increased in number after the autoclave treatment. It is reasonable to think from this result that a great number of the foreign matters would fall from the syringe formed from plastic, on which a silicone coating cannot be baked.

On the contrary, it has been observed that few silicone foreign matters has fallen from the syringes of-the first and second embodiments. The reason for this would be the inexistence of silicone coating at any portions of each syringe contacting the dust free distilled water filled in the syringe.

Example 2

As Example 2, the testing was conducted to confirm the slidability of the seal. As a reference for judging the degree of the slidability, the load required for the initial sliding movement of the seal (initial sliding resistance value) and the maximum load required for expelling the fluid (maximum sliding resistance value) were measured.

In this example, the respective loads were measured by using the syringe of the first embodiment formed from plastic was used, in which the seal having a diameter of 15 mm, a height of 10 mm, and three larger diameter portions was forced into the syringe, and was filled with dust-free distilled water of 5 ml.

The results measured before and after the autoclave treatment for each quantity of silicone applied onto the seal will be shown in TABLES 3 and 4.

TABLE 3

| | Quantity of Silicone Applied | Before Autoclave Treatment | |
|---|---|---|---|
| | | initial sliding resistance value (gf) | maximum sliding resistance value (gf) |
| Embodiment 1 | 1 (μl) | 873 | 543 |
| | 2 (μl) | 820 | ≈0 |
| | 3 (μl) | 817 | ≈0 |
| | 4 (μl) | 793 | ≈0 |

Testing Device: Shimazu Auto Graph S-500
Sliding Speed: 25 mm/min.

TABLE 4

| | Quantity of Silicone Applied | After Autoclave Treatment | |
|---|---|---|---|
| | | initial sliding resistance value (gf) | maximum sliding resistance value (gf) |
| Embodiment 1 | 1 (μl) | 821 | 459 |
| | 2 (μl) | 777 | 240 |
| | 3 (μl) | 780 | ≈0 |
| | 4 (μl) | 808 | ≈0 |

Testing Device: Shimazu Auto Graph S-500
Sliding Speed: 25 mm/min.

As comparative examples, the initial load resistance value was measured under the same conditions applied in this Example by using commercially available disposable syringes F to J, each having silicone applied onto the entire surface of the inner wall thereof. The measured results are shown in TABLE 5.

TABLE 5

| | initial sliding resistance value (gf) | maximum sliding resistance value (gf) |
|---|---|---|
| Sample F | 1196 | ≈0 |
| Sample G | 633 | ≈0 |
| Sample H | 1270 | ≈0 |
| Sample I | 519 | ≈0 |
| Sample J | 696 | ≈0 |

Testing Device: Shimazu Auto Graph S-500
Sliding Speed: 25 mm/min.

As being apparent from TABLE 3 to 5, it has been confirmed that the seal of each syringe according to the present invention exhibit the same degree of slidability as that of each conventional disposable syringe with silicone applied onto the entire surface of its inner wall.

This specification is by no means intended to restrict the present invention to the preferred embodiments set forth therein. Various modifications to the syringe, the syringe assembly and the apparatus of the present invention, as described herein, may be made by those skilled in the art without departing from the spirit and scope of the present invention as defined in the appended claims.

What is claimed is:

1. An apparatus for manufacturing a syringe including a tubular barrel having an open proximal end, a distal end with a fluid expelling passage defined therein, and a barrel chamber, a seal being disposed within said barrel chamber a predetermined distance away from said open proximal end in fluid-tight and axially-sliding engagement with said barrel chamber, said seal defining at least two diametrically enlarged portions at axially spaced apart portions on said seal so as to be respectively in abutment with the inner wall of said barrel chamber and a concave portion between adjacent diametrically enlarged portions of said at least two diametrically enlarged portions for defining a clearance relative to said inner wall of said barrel chamber, wherein lubricant film exists at interfaces between said at least two diametrically enlarged portions of said seal and said inner wall of said barrel chamber, and lubricant is filled in said clearance, said apparatus comprising:

a barrel retaining unit for retaining said barrel of said syringe therein;

a seal detent unit defining therein a through-hole having an inner diameter substantially equal to the outer diameter of said seal for holding said seal at a detent position within said through-hole, a diametrically smaller tubular portion in which one open end of said through-hole is defined, said diametrically smaller tubular portion being capable of plunging into said barrel chamber via said open proximal end of said barrel and passing a predetermined distance away from said open proximal end of said barrel, and a passage in communication between said detent position of said through-hole and the outside of said seal detent unit for feeding lubricant from said outside to said seal held at said detent position of said through-hole; and a thrusting unit for forcing said seal held within said through-hole of said seal detent unit out of said through-hole via an opening of said diametrically smaller tubular portion of said seal detent unit;

whereby said diametrically smaller tubular portion of said seal detent unit is plunged into said barrel chamber of said syringe, and then said seal with lubricant applied onto said at least two diametrically enlarged portions thereof and filled in said clearance via said passage is forced into said barrel chamber by said thrusting unit as said diametrically smaller tubular portion remains within said barrel chamber.

* * * * *